United States Patent [19]

Greuter et al.

[11] 4,234,517
[45] Nov. 18, 1980

[54] 2-(2',2'-DIHALOVINYL)-CYCLOBUTA-NONES AND 2-(2',2',2'-TRIHALOETHYL)-CYCLOBUTA-NONES

[75] Inventors: Hans Greuter, Eiken; Pierre Martin, Basel; Daniel Bellus, Riehen, all of Switzerland

[73] Assignee: Ciba-Geigy Corporation, Ardsley, N.Y.

[21] Appl. No.: 21,273

[22] Filed: Mar. 16, 1979

Related U.S. Application Data

[62] Division of Ser. No. 891,413, Mar. 29, 1978, abandoned.

[30] Foreign Application Priority Data

Mar. 31, 1977 [CH] Switzerland .......................... 4072/77
Feb. 23, 1978 [CH] Switzerland .......................... 1975/78

[51] Int. Cl.³ .............................................. C07C 49/39
[52] U.S. Cl. .................................. 568/381; 260/343.6
[58] Field of Search ............ 260/586 R, 586 G, 593 H

[56] References Cited

U.S. PATENT DOCUMENTS 4,028,418  6/1977  van den Brink et al. ....... 260/586 R

FOREIGN PATENT DOCUMENTS 2654060  3/1978  Fed. Rep. of Germany .
1194604  11/1967  United Kingdom .

OTHER PUBLICATIONS

Elliott, M. et al., "Potent Pyrethroid Insecticides from Modified Cyclopropane Acids," Nature, vol. 244 (Aug. 17, 1973) p. 45617.
J. of the American Chemical Society, vol. 87, pp. 5257-5259 (1965).
Tetrahedron Letters, No. 1, pp. 135-139 (1966).
Heine, Hans Georg et al., Ger. Offen. No. 2,638,356, Mar. 2, 1978, (See Chemical Abstracts, vol. 88, #190, 209n (1978).

Primary Examiner—Natalie Trousof
Assistant Examiner—L. Hendriksen
Attorney, Agent, or Firm—Harry Falber

[57] ABSTRACT

Novel 2-(2',2'-dihalovinyl)-cyclobutan-1-ones and 2-(2',2',2'-trihaloethyl)-cyclobutan-1-ones of the formula

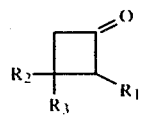

are disclosed, wherein $R_1$ represents $-CH \cdot CX_2$ or $-CH_2-CX_3$, and X in each case represents chlorine or bromine, one of $R_2$ and $R_3$ represents methyl and the other represents hydrogen or methyl, or $R_2$ and $R_3$ together represent an alkylene group having 2 to 4 carbon atoms. The invention relates also to the production and the use of the said cyclobutanones.

2 Claims, No Drawings

2-(2',2'-DIHALOVINYL)-CYCLOBUTANONES AND 2-(2',2',2'-TRIHALOETHYL)-CYCLOBUTANONES

This is a divisional of application Ser. No. 891,413 filed on Mar. 29, 1978, now abandoned.

The present invention relates to novel 2-(2',2'-dihalovinyl)-cyclobutan-1-ones and 2-(2',2',2'-trihaloethyl)-cyclobutan-1-ones, to a process for producing them, and also to their use for producing 2-(2',2'-dihalovinyl)-cyclopropanecarboxylic acids and esters thereof.

The novel 2-(2',2'-dihalovinyl)-cyclobutan-1-ones and 2-(2',2',2'-trihaloethtyl)-cyclobutan-1-ones correspond to the formula I

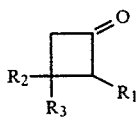

wherein
$R_1$ represents —CH=CX$_2$ or —CH$_2$—CX$_3$, and X in each case represents chlorine or bromine,
one of $R_2$ and $R_3$ represents methyl and the other hydrogen or methyl, or
$R_2$ and $R_3$ together represent alkylene having 2-4 C atoms.

The symbol X preferably represents chlorine. Of $R_2$ and $R_3$, one is preferably methyl and the other hydrogen or methyl, or $R_2$ and $R_3$ together represent alkylene having 2 or 3 C atoms.

The compounds of the formula I can be obtained by reacting a compound of the formula II

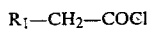

in the presence of an organic base, with a compound of the formula III

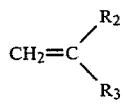

wherein $R_1$, $R_2$ and $R_3$ have the meanings given under the formula I.

Aldoketenes of the formula IV

are formed in situ in the process. These aldoketenes of the formula IV are novel. It is very surprising that 2+2-cycloadducts are formed by the process according to the invention, since aldoketenes generally dimerise in the presence of tertiary amines, and do not usually undergo 2+2-cycloaddition reactions with olefins which are not conjugated, especially with olefins of the formula III.

The compounds of the formula II and III are known, or can be produced in a manner known per se [see, e.g., J. Ray and R. Vessière, Bull. Soc. Chim. France, 269–71 (1967), U.S. Pat. Nos. 3,309,403, 3,423,456, 3,361,811 and 3,484,482, and also Tetrahedron Letters, 913–915 (1968)]. Compounds of the formula II wherein $R_1$ represents —CH=CX$_2$ can be produced by a novel process also by reacting a lactone of 3-hydroxy-4,4,4-trihalobutyric acid [see German Pat. No. 1,214,211], in the presence of an aliphatic monocarboxylic acid having 1-3 C atoms in the acid part, such as formic acid, acetic acid or propionic acid, and in the presence of reducing agents such as zinc powder, iron powder or tin powder, to the corresponding 4,4-dihalobut-3-enecarboxylic acids, and subsequently chlorinating these with, e.g., thionyl chloride, oxalyl chloride, phosphorus trichloride or phosphorus pentachloride.

The reaction of the acid chlorides of the formula II with the olefins of the formula III is performed as defined in the presence of an organic base, and preferably in the presence of an inert organic solvent. Suitable inert organic solvents which can be used are, for example, optionally halogenated, particularly chlorinated, aromatic, aliphatic or cycloaliphatic hydrocarbons, such as benzene, toluene, xylenes, chlorobenzene, n-pentane, n-hexane, n-octane, cyclopentane or cyclohexane, chloroform or trichloroethylene; aliphatic or cycloaliphatic ketones such as acetone, methyl ethyl ketone, di-isopropyl ketone, cyclopentanone and cyclohexanone; aliphatic and cyclic ethers such as diethyl ether, tetrahydrofuran, tetrahydropyrane and dioxane; and nitriles of saturated aliphatic monocarboxylic acids having a total of 1–6 carbon atoms, such as acetonitrile, propionitrile, methoxypropionitrile and butyronitrile.

Aliphatic, cycloaliphatic and aromatic hydrocarbons are preferred, particularly alkanes having 5–8 carbon atoms, cyclopentane, cyclohexane, benzene and toluene.

The reaction can however also be performed without addition of an inert organic solvent.

Orgaic bases which can be used are, e.g., tertiary amines, particularly trialkylamines having in each alkyl moiety 1–4, especially 2–4, carbon atoms; cyclic amines, such as pyridine, quinoline, N-alkyl-pyrrolidines, N-alkyl-piperidines, N,N'-dialkyl-piperazines and N-alkyl-morpholines or dialkylanilines, having in each alkyl moiety 1 or 2 carbon atoms, such as N-methylpyrrolidine, N-ethylpiperidine, N,N'-dimethylpiperazine, N-ethylmorpholine and dimethylaniline, and also bicyclic amidines, such as 1,5-diazabicyclo[5.4.0]undec-5-ene and 1,5-diazabicyclo[4.3.0]non-5-ene and bicyclic amino compounds such as 1,4-diazabicyclo[2.2.2]octane.

Preferred bases are trialkylamines having in each alkyl moiety 2–4 carbon atoms, particularly triethylamine, and pyridine. The organic base can simultaneously serve as solvent.

The reaction temperatures are in general between about 0° and 140° C., preferably between about 60° and 120° C.

The acid chloride of the formula II and the olefin of the formula III are used advantageously in at least a stoichiometric amount. There is preferably used an excess of the olefin of the formula III, with the olefin then serving also as solvent.

The organic base is used advantageously in a slight excess over the stoichiometrically required amount, preferably in an approximately 5–30% molar excess. If the organic base at the same time serves as solvent, it is advantageously used in an approximately 10–20-fold molar excess.

The compounds of the formula I can be produced also by a modified process in which an acid chloride of the formula V

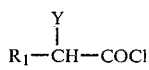
(V)

is reacted, in the presence of an organic base of the aforementioned type, with an olefin of the formula III to give a compound of the formula VI

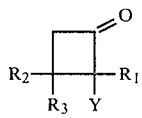
(VI)

wherein Y has the same meaning as X or represents, where X is chlorine, also bromine, and the compound of the formula VI is converted, in the presence of a reducing agent, into a compound of the formula I.

The reaction to compounds of the formula VI is performed advantageously in an inert organic solvent, e.g. in a solvent of the aforementioned type, at temperatures of between about 0° and 150° C., preferably between about 20° and 100° C. The reducing agent used can be, for example, zinc, tin or iron in elementary form. The reduction is carried out advantageously in an anhydrous aliphatic monocarboxylic acid having 1-3 C atoms in the acid part, such as anhydrous formic and propionic acid, preferably glacial acetic acid.

The acid chlorides of the formula V wherein $R_1$ represents —$CH_2$—$CX_3$ are novel. They can be produced for example by performing an addition reaction of a compound of the formula VII $$CX_3-Y \quad (VII),$$

wherein X and Y each represent chlorine or bromine, or X represents chlorine and Y represents bromine, in the presence of a catalyst, such as copper powder, iron powder, copper halides and iron halides, particularly chlorides and bromides of copper and of iron, or mixtures thereof, and in the presence of an organic solvent, such as alkyl nitriles having 1-6 C atoms in the alkyl moiety or 3-alkoxypropionitriles having 1 or 2 C atoms in the alkoxy moiety, with acrylic acid chloride; or, in the case where X and Y each represent chlorine, an addition reaction of a compound of the formula VIIa $$Cl_2CH-Z \quad (VIIa)$$

wherein Z represents —COCl, COOH, —COOalkyl having 1-4 C atoms in the alkyl moiety, or —CN, in the presence of a catalyst mentioned above, and in the presence of an organic solvent, with 1,1-dichloroethylene; and converting intermediates of the formula VIIb

(VIIb)

wherein Z represents —COOH, —COOalkyl having 1-4 C atoms in the alkyl moiety, or —CN, in a manner know per se, into a compound of the formula V.

The resulting compound of the formula V with $R_1$=—$CH_2CX_3$ can be converted into the corresponding acid chloride with $R_1$=—CH=$CX_2$ by, for example, HX-elimination in the presence of iron(III)chloride. The stated acid chlorides of the formula V with $R_1$=—CH=$CX_2$ are described generically in the U.S. Pat. No. 3,423,456.

After the reaction has finished, the compounds of the formula I can be isolated and purified in a manner known per se, e.g. by filtration, concentration by evaporation, and distillation.

The compounds of the formula I are valuable intermediates for producing pesticidal compositions. The said compounds can also be converted by a novel, altogether unique, synthesis into pyrethroid-like pesticidal compositions or into precursors thereof.

The present invention relates therefore also to the use of the compounds of the formula I for producing compounds of the formula VIII

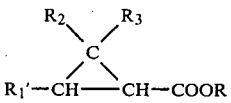
(VIII)

wherein
$R_1'$ represents —CH=$CX_2$,
X, $R_2$ and $R_3$ have the meanings given under the formula I, and
R represents alkyl having 1-4 C atoms, or a grouping of the formula

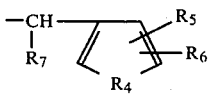

in which
$R_4$ represents —O—, —S— or —CH=CH—,
$R_5$ represents hydrogen, alkyl having 1-4 C atoms, benzyl, phenoxy or phenylmercapto,
$R_6$ represents hydrogen or alkyl having 1-4 C atoms, and
$R_7$ represents hydrogen or ethynyl, or, if one of $R_2$ and $R_3$ represents methyl and the other represents hydrogen or methyl, $R_4$ represents —CH=CH—, $R_5$ represents phenoxy and
$R_6$ represents hydrogen,
and R also represents alkyl having 1-5 C atoms,
by oxidising a compound of the formula I to a compound of the formula IX

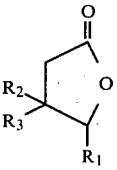
(IX), halogenating the compound of the formula IX, and reacting the halogenated compound with an agent introducing the radical R, with R, $R_1$, $R_2$ and $R_3$ having the meanings given in the foregoing.

The oxidising agents used can be compounds known per se, e.g. inorganic or organic peroxides, such as hydrogen peroxide, potassium peroxydisulphate, tert-butylhydroperoxide, di-tert-butyl peroxide, peracetic acid, trifluoroperacetic acid, benzoyl peroxide, m-chloroperbenzoic acid, perphthalic acid, cumenehydroperoxide, tert-butylperbenzoate, tert-butylperacetate and methyl ethyl ketone peroxide.

The oxidising agent is preferably used in an equimolar amount or in a slight excess, relative to the compound of the formula VIII.

The oxidation is advantageously performed in an inert organic solvent, such as optionally halogenated aliphatic or aromatic hydrocarbons, e.g. methylene chloride, chloroform, 1,2-dichloroethane, carbon tetrachloride, trichloroethylene, 1,1,2,2-tetrachloroethane, benzene, toluene, xylenes, chlorobenzene, dichlorobenzenes and trichlorobenzenes; or in an aliphatic monocarboxylic acid, such as acetic acid, or in water.

The reaction temperatures for the oxidation are in general between about 0° and 60° C., preferably between about 20° and 50° C.

Suitable halogenating agents for the halogenation of the lactone of the formula IX are, for example: hydrohalic acids such as HCl and HBr, and aprotic halogenating agents, such as phosphorus pentachloride, thionyl chloride, thionyl bromide, phosphorus trichloride, phosphorus tribromide and oxalyl chloride. Preferred halogenating agents are HCl, HBr and thionyl chloride.

The halogenation and the reaction with an agent introducing the radical R can be performed for example as follows:

(a) The compound of the formula IX is mixed together with a compound of the formula X

ROH            (X)

wherein R has the meaning given in the foregoing, and preferably represents alkyl having 1–4 C atoms; the mixture is saturated with a hydrohalic acid as halogenating agent; and, after removal of the unreacted hydrohalic acid, subsequently reacted with an acid-binding agent. The acid-binding agents employed can be, for example, alkali metal alcoholates of the formula XI

ROM            (XI)

wherein R has the meaning given in the foregoing, and preferably represents alkyl having 1–4 C atoms, and M represents an alkali metal, particularly sodium or potassium. Suitable acid-binding agents are also hydrides of alkali metals and alkaline-earth metals, especially hydrides of sodium, potassium and calcium.

The compound of the formula X is used in at least stoichiometric amounts, preferably however in excess, optionally diluted with an inert organic solvent, such as aromatic, aliphatic or cycloaliphatic hydrocarbons, or aliphatic and cyclic ethers of the type mentioned in the foregoing.

(b) The compound of the formula IX is firstly treated with an aprotic halogenating agent, and afterwards are added at least stoichiometric amounts of a compound of the formula X, optionally in the presence of tertiary amines and optionally also in the presence of an inert organic solvent of the aforementioned type; and subsequently the mixture is treated with an acid-binding agent of the type mentioned under (a).

(c) The compound of the formula IX is firstly treated with an aprotic halogenating agent, optionally in the present of an inert organic solvent of the type mentioned in the foregoing, and the mixture is subsequently reacted with a compound of the formula XI. In this case, the compound of the formula XI acts simultaneously as agent introducing the radical R and as acid-binding agent.

The halogenating agents and the compounds of the formulae X and XI, which introduce the radical R, are used in at least the stoichiometrically required amount, preferably however in excess. The halogenation and the reaction for introducing the radical R to give compounds of the formula VIII are advantageously performed at temperatures of between about 0° and 100° C., usually between about 20° and 80° C., under normal or elevated pressure.

In consequence of the reaction of the acid-binding agent in the conversion of the lactones of the formula IX to the cyclopropanecarboxylic acid derivatives of the formula VIII, trihaloethyl groups $R_1$ are transformed into the corresponding dihalovinyl groups.

The compounds of the formula VIII can be obtained as cis- or trans-isomers (with regard to the COOR group and the dihalovinyl group), or as mixtures of cis/trans isomers. The mixtures can be separated by known methods into the individual isomers.

By way of the novel cyclobutanones of the formula I according to the invention, the compounds of the formula VIII can be produced by a process which is new, and quite remarkable compared with processes known hitherto, in a particularly simple and economic manner, in good yields and under mild reaction conditions, and also without great expenditure on apparatus or on measures to ensure technical safety.

Compounds of the formula VIII wherein R represents alkyl having 1–4 C atoms can be converted, in a manner known per se, into active substances of the formula VIII with R≠alkyl having 1–4 C atoms, for example by reaction with corresponding alcohols or halides [see, e.g., German Offenlegungsschriften Nos. 2,553,991 and 2,614,648].

Compounds of the formula VIII with R≠alkyl having 1–4 C atoms are suitable for combating the widest variety of animal and plant pests; particularly where the compounds are used as insecticides. The properties, fields of application and forms of application of these active substances are described in the literature [see, e.g., Nature, 246, 169–70 (1973); Nature, 248, 710–11 (1974); Proceedings 7th British Insecticide and Fungicide Conference, 721–28 (1973); Proceedings 8th British Insecticide and Fungicide Conference, 373–78 (1975); J. Agr. Food Chem., 23, 115 (1975); U.S. Pat. Nos. 3,961,070 and 3,987,193; and German Offenlegungsschriften Nos. 2,553,991, 2,439,177, 2,326,077 and 2,614,648].

EXAMPLE 1

84 g (1.5 mols) of isobutylene and 10.0 g (0.099 mol) of triethylamine are heated in an autoclave to 120° C. A solution of 17.35 g (0.1 mol) of 4,4-dichlorobut-3-enecarboxylic acid chloride in 35 ml of diethyl ether is then injected in the course of 30 minutes, and the reaction mixture is stirred at 120° C. for 2 hours. After cooling, the reaction mixture is triturated with diethyl ether. Solid constituents are filtered off, and the filtrate is subsequently washed with 1 N sulphuric acid (2×30 ml) as well as with 1% sodium bicarbonate solution (3×50 ml). After drying over sodium sulphate, concentration by evaporation is performed, and the residue is distilled in a bulb tube to yield 2-(2′,2′-dichlorovinyl)-3,3-dimethylcyclobutanone as colourless oil; b.p. 100°–110° C./0.5 Torr.

IR Spectrum (film): 3010, 2970, 2930, 2810, 1788, 1615, 923, 870 cm$^{-1}$.

NMR Spectrum (100 MHz, CDCl$_3$) in ppm: 5.85 (d, 1H); 3.95 (dxdxd; 1H); 3.00 (dxd, 1H); 2.60 (dxd, 1H); 1.54 (s, 3H); 1.20 (s, 3H).

The 4,4-dichlorobut-3-ene-1-carboxylic acid chloride used as starting product can be produced as follows: 200 g (1.055 mols) of lactone of 3-hydroxy-4,4,4-trichlorobutyric acid (produced according to German Pat. No. 1,214,211) is dissolved in 625 ml of formic acid. The solution obtained is heated to 55° C. and stirred. After removal of the heating source, zinc powder is introduced in smallish portions in the course of 1 hour. The temperature of the reaction mixture is held at 60° C. by means of external cooling. After introduction of the zinc powder, the reaction mixture is stirred for a further 90 minutes, cooled and filtered. 400 ml of formic acid is distilled off from the filtrate; the residue is diluted with 1 liter of water, and extracted with four 200 ml portions of diethyl ether. The ether extracts are dried over magnesium sulphate, and the solvent is removed by distillation. The colourless residue (152 g) solidifies to a crystalline mass of 4,4-dichlorobut-3-ene-1-carboxylic acid; m.p. 39°–41° C. [see J. Ray and R. Vessière, Bull. Soc. Chim. France, 269 (1967), where a m.p. of 40°–41° C. is given for 4,4-dichlorobut-3-ene-1-carboxylic acid].

IR Spectrum (CHCl$_3$): inter alia 1732 (C=O), 1635 (C=C) cm$^{-1}$.

NMR Spectrum (CDCl$_3$) in ppm: 3.30 (d, J=7 Hz, CH$_2$—2); 6.09 (d, CH-3); 11.37 (s, —COOH).

4,4-Dichlorobut-3-ene-1-carboxylic acid can also be obtained by firstly converting the lactone of 3-hydroxy-4,4,4-trichlorobutyric acid by hydrolysis with water into 4,4,4-trichloro-3-hydroxybutyric acid [m.p. 117°–118° C.; IR Spectrum (CHCl$_3$) inter alia 1730 (C=O) cm$^{-1}$; NMR Spectrum (CDCl$_3$) in ppm: 2.4–3.3 (m, CH$_2$—2); 4.4–4.7 (m, CH-3) and 6.0–7.0 (broad, s, —OH and —COOH], and then treating a solution of this butyric acid in formic acid as described above.

152 g of the 4,4-dichlorobut-3-ene-1-carboxylic acid is stirred with 140 g of thionyl chloride for 2 hours. The subsequent distillation yields 152.3 g of 4,4-dichlorobut-3-ene-1-carboxylic acid chloride; b.p. 62° C./15 Torr [b.p. 64°–65° C./11 Torr according to J. Ray and R. Vessière, Bull. Soc. Chim. France, 269 (1967)].

EXAMPLE 2

1.93 g (0.01 mol) of the 2-(2',2'-dichlorovinyl)-3,3-dimethylcyclobutanone produced according to Example 1 is placed into 20 ml of methylene chloride, and 2 g (0.012 mol) of m-chloroperbenzoic acid is added portionwise. The reaction mixture is subsequently stirred for 2 hours at room temperature (20°–25° C.), filtered, and then washed with methylene chloride. The filtrate is washed with sodium carbonate solution and water, dried over magnesium sulphate and concentrated by evaporation. The residue (1.9 g) is distilled in a bulb tube (oven temperature 70° C.) at 0.03 mm Hg. There is thus obtained the lactone of 3,3-dimethyl-4-hydroxy-6,6-dichlorohex-5-enecarboxylic acid as light-yellow oil having a boiling point of 135° C./5 Torr.

IR Spectrum (CHCl$_3$) in cm$^{-1}$: 1785 (C=O); 1630 (C=C).

$^1$H-NMR Spectrum (100 MHz, in CHCl$_3$) in ppm: 1.14 and 1.29 (each 1 s, each 3H, each CH$_3$); 2.04 (AB system, 2H, CH$_2$); 4.10 (d, J=9.5 Hz, 1H); 4.94 (d, J=9.5 Hz, 1H).

Analysis for C$_8$H$_{10}$Cl$_2$O$_2$ (molecular weight 209.17): calculated: C 45.96%, H 4.82%, O 15.31%, Cl 33.97%. found: C 45.8%, H 4.7%, O 15.5%, Cl 33.8%.

EXAMPLE 3

Dry HCl is introduced into 5.25 g (0.025 mol) of the lactone of 3,3-dimethyl-4-hydroxy-6,6-dichlorohex-5-enecarboxylic acid dissolved in 40 ml of absolute ethanol. After the reaction has subsided (temperature rise 40°–60° C.), the reaction mixture is concentrated by evaporation; it is taken up in absolute ethanol, and 0.025 mol of sodium ethylate (produced from 0.6 g of sodium in ethanol) is added. After 30 minutes' stirring, the mixture is concentrated by evaporation; water is then added, the mixture is rendered acid with hydrochloric acid and extracted with diethyl ether. The extracts are dried over magnesium sulphate and concentrated by evaporation, and the residue is distilled to yield the compound of the formula

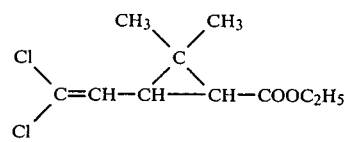

as a colourless liquid having a boiling point of 50° C./0.035 Torr.

IR Spectrum (CHCl$_3$) in cm$^{-1}$: 1725 (C=O); 1620 (C=C).

$^1$H-NMR Spectrum (CDCl$_3$) in ppm: 1.23 (s); 1.31 (s) and 1.33 (t, J=7 Hz, each CH$_3$, total 9H); 1.64 (d, J=5 Hz, 1H, H—C(1)); 2.26 (dd, J=5 and 8.5 Hz, 1H, H—C(3)); 4.16 (q, J=7 Hz, CH$_2$); 5.61 (d, J=8.5 Hz, 1H, C=CH of the trans compound); 6.27 (d, J=8.5 Hz, 0.2H, C=CH of the cis compound).

The cis-trans ratio is accordingly about: 1:5.

EXAMPLE 4

Example 3 is repeated except that dry hydrogen bromide is introduced instead of HCl. 2-(2',2'-Dichlorovinyl)-3,3-dimethylcyclopropanecarboxylic acid ethyl ester with a cis/trans ratio of approximately 4, determined according to NMR spectrum as in Example 3, is obtained in almost quantitative yield.

EXAMPLE 5

5.25 g (0.025 mol) of the lactone of 3,3-dimethyl-4-hydroxy-6,6-dichlorohex-5-enecarboxylic acid with 15 ml of thionyl chloride is held for 3 hours at 70° C. An addition of 20 ml of ethanol is then made, and the reaction mixture is allowed to stand for 14 hours at room temperature. The reaction mixture is concentrated by evaporation, and the residue is treated briefly with sodium ethylate in ethanol, as described in Example 3. After customary processing, there is obtained in 81% yield the 2-(2',2'-dichlorovinyl)-3,3-dimethylcyclopropanecarboxylic acid ethyl ester having a cis-trans ratio of approximately 1:4, determined according to NMR spectrum.

EXAMPLE 6

5.25 g (0.025 mol) of the lactone of 3,3-dimethyl-4-hydroxy-6,6-dichlorohex-5-enecarboxylic acid and 20 ml of thionyl chloride are held for 3 hours at 70° C. The cooled reaction mixture is concentrated by evaporation; a solution of 6 g of m-phenoxybenzyl alcohol in 30 ml of absolute benzene is added, and the temperature is raised to 50° C. A suspension of 5.4 g of potassium-tert-butylate in 20 ml of absolute benzene is added in the course of one hour. The mixture is stirred for one hour, and water is then carefully added; the mixture is subsequently acidified with hydrochloric acid, and the organic phase is separated. After concentration by evaporation, the crude product is chromatographed, with diethyl ether/n-hexane as eluant (1:4 volume ratio), through silica gel to obtain the compound of the formula

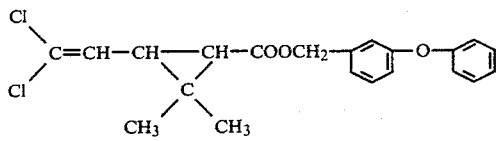

having a refractive index of $n_D^{20} = 1.563$.

EXAMPLE 7

26.4 g (0.1 mol) of 2-chloro-2-(2',2',2'-trichloroethyl)-3,3-dimethylcyclobutanone is placed into 150 ml of glacial acetic acid, and 13 g (0.2 mol) of zinc dust is added portionwise in such a way that the temperature does not exceed 40° C. The reaction mixture is then stirred for one hour at 30° C., filtered, and washed with diethyl ether. The filtrate is carefully concentrated by evaporation; water is added and the mixture is extracted with diethyl ether. The organic phase is washed with water, with aqueous sodium carbonate solution and again with water; it is subsequently dried over magnesium sulphate and concentrated by evaporation. The residue is distilled at 121°-123° C./15 mm Hg to yield 2,-(2',2',2'-trichloroethyl)-3,3-dimethylcyclobutanone as a clear liquid.

IR Spectrum (CHCl₃): 1785 cm⁻¹ (C=O).

¹H-NMR Spectrum (100 MHz, CDCl₃) in ppm: 1.23 and 1.58 (each 1 s, each 3H, each CH₃); 2.50-3.20 (m, 4H, α—CH₂ and CH₂—(4)); 3.45 (1H, CH—(2)).

¹³C-NMR Spectrum (CDCl₃) in ppm: 204.9 (s, CO); 95.2 (s, CCl₃); 64.8 (d, C-2); 58.4 (t, C-4); 50.1 (t, CH₂); 30.5 (s, C-3); 29.3 (q, CH₃ trans with respect to CH₂—CCl₃); 23.2 (q, CH₃ cis with respect to CH₂—CCl₃).

The 2-chloro-2-(2',2',2'-trichloroethyl)-3,3-dimethylcyclobutanone used as starting product can be produced as follows: 452.5 g (5 mols) of acrylic acid chloride (commercial degree of purity), 1.5 liters of carbon tetrachloride, 1.5 liters of acetonitrile and 30 g of copper(I)chloride are kept at 115° C. for 24 hours. The reaction mixture is filtered, and distilled in a water-jet vacuum to thus obtain 922 g (76% of theory) of 2,4,4,4-tetrachlorobutanecarboxylic acid chloride in the form of a clear liquid having a boiling point of 78°-80°/11 mm Hg.

IR Spectrum (CHCl₃): 1780 cm⁻¹ (C=O).

NMR Spectrum (CDCl₃) in ppm: 3.16-3.94 (CH₂); 5.08 (CH).

Mass spectrum: 207 (M), 179 (M⁺—COCl), 171 (M⁺—HCl).

280 g of isbutylene is injected into an autoclave containing 122 g (0.5 mol) of the above 2,4,4,4-tetrachlorobutanecarboxylic acid chloride in 600 ml of cyclohexane. There is then pumped in at 65° C., in the course of 4 hours, 51 g (0.5 mol) of triethylamine in 500 ml of cyclohexane. The reaction mixture is then kept at 65° C. for a further 3 hours. The precipitated hydrochloride of the triethylamine is filtered off, and subsequently washed with cyclohexane. The filtrate is concentrated by evaporation, and the crystals resulting are filtered off. There is obtained 79.4 g of 2-chloro-2-(2',2',2'-trichloroethyl-3,3-dimethylcyclobutanone; m.p. 75°-76° C.

IR Spectrum (CHCl₃): 1805 cm⁻¹ (C=O).

¹H-NMR Spectrum (CDCl₃) in ppm: 3.50 (CH₂); 3.05 (CH₂); 1.42 and 1.45 (each 1 s, each 3H, each CH₃).

¹³C-NMR-Spectrum (CDCl₃) in ppm; 196.6 (s, CO); 95.3 (s, CCl₃); 80.8 (s, C-2); 57.0 (t, CH₂); 56.4 (t, CH₂); 37.9 (s, C-3); 25.1 (q, CH₃); 23.8 (q, CH₃).

Elementary analysis for C₈H₁₀Cl₄O (molecular weight 263.98): calculated: C 36.40%, H 3.82%, O 6.02%, Cl 53.72%. found: C 36.4%, H 3.9%, O 6.2%, Cl 53.5%.

EXAMPLE 8

15.3 g (0.067 mol) of 2-(2',2',2'-trichloroethyl)-3,3-dimethylcyclobutanone, 75 ml of glacial acetic acid and 7.6 g of a 30% aqueous H₂O₂ solution are placed together and stirred at 35° C. for 3.5 hours. The mixture is then vigorously stirred up with water containing iron-(III)chloride until no further peroxide is detectable. The resulting mixture is extracted with n-hexane. The extract is dried over magnesium sulphate and concentrated by evaporation. The residue (13.4 g) is distilled to yield the lactone of 3,3-dimethyl-4-hydroxy-6,6,6-trichlorohexanecarboxylic acid as a clear liquid; b.p. 108°-111° C./0.3 mm Hg.

IR Spectrum (CHCl₃): 1810 cm⁻¹ (C=O).

¹H-NMR Spectrum (100 MHz, CDCl₃) in ppm: 1.12 and 1.29 (each 1 s, each 3H, each CH₃); 2.43 (2H, CH₂—(2)); 2.87-3.20 (2H, CH₂—(5)); 4.49 (1H, CH—4).

EXAMPLE 9

10.2 g (0.042 mol) of the lactone of 3,3-dimethyl-4-hydroxy-6,6,6-trichlorohexanecarboxylic acid is stirred up for 40 hours in 150 ml of absolute ethanol which is saturated with hydrobromic acid. The reaction solution is concentrated by evaporation; it is taken up twice in absolute toluene and again concentrated by evaporation. The residue is introduced into a suspension of toluene (150 ml) and potassium-tert-butylate (10.3 g), and vigorous stirring is maintained for 2 hours at room temperature. The reaction mixture is subsequently refluxed for 5 hours and then allowed to stand overnight (room temperature). It is then acidified with dilute hydrochloric acid, and the organic phase is separated. The aqueous phase is extracted with diethyl ether. The ether extracts are combined with the organic phase, and the whole is washed with concentrated NaCl solution, dried over magnesium sulphate and concentrated by evaporation. The residue is filtered through silica gel (toluene/ethyl acetate as eluant in the volume ratio of 15:1), and the filtrate is again concentrated by evaporation. Distillation yields a yellow oil having a boiling point of 72°-74° C./0.2 mm Hg. The spectroscopic data of the resulting substance (IR, NMR) are indentical with that of the substance obtained according to Example 3. The cis/trans ratio of the ethyl esters of 2,2-dimethyl-3-(2',2'-dichlorovinyl)-cyclopropanecarboxylic acid, measured from the NMR spectrum, is approximately 5:1.

EXAMPLE 10

18 g of 1-chloro-1-(2',2',2'-trichloroethyl)spiro(3.3)-heptan-2-one is placed into 200 ml of formic acid, and 8.5 g of zinc dust is added portionwise in such a way that the temperature does not exceed 30° C. The reaction mixture is afterwards stirred for two hours at 30° C. and then filtered. The filtrate is concentrated by evaporation; water is added and the mixture is extracted with diethyl ether. The ethereal phase is washed with water, with aqueous sodium carbonate solution and again with water; it is dried over sodium sulphate and concentrated by evaporation. The residue is distilled at 75°–80° C./0.03–0.05 Torr to yield 1-(2',2',2'-trichloroethyl)-spiro(3.3)heptan-2-one of the formula

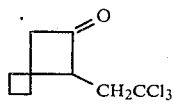

as a clear liquid.

IR Spectrum (fl.): 1788 cm$^{-1}$ (C=O).

$^1$H-NMR Spectrum (100 MH$_2$, CDCl$_3$) in ppm: 1.7–3.2 (m, 10H); 3.4–3.6 (m, 1H, CH—(1).

The 1-chloro-1-(2',2',2'-trichloroethyl)spiro(3.3)heptan-2-one used as starting product can be produced as follows:

145.9 g (1.5 mols) of 1,1-dichloroethylene, 147.4 g (1 mol) of dichloroacetyl chloride, 200 ml of acetonitrile and 3 g of copper(I)chloride are heated at 130° C. for 8 hours. The reaction mixture is concentrated by evaporation, and the residue is fractionally distilled to yield 2,4,4,4-tetrachlorobutyric acid chloride as a colourless liquid, b.p. 78°–80° C./11 mm Hg.

IR Spectrum (CHCl$_3$) in cm$^{-1}$: 1780 (CO).

NMR Spectrum (100 MHz, CDCl$_3$) in ppm: 3.16–3.94 (m, 2H, CH$_2$); 4.84–4.96 (m, 1H, CH).

A solution of 25.3 g (0.25 mol) of triethylamine in 50 ml of n-hexane is added dropwise in the course of 7 hours, with stirring, to a solution, kept under reflux, of 25 g (0.37 mol) of methylenecyclobutane and 61.1 g (0.25 mol) of 2,4,4,4-tetrachlorobutyric acid chloride in 200 ml of hexane. After a further 2 hours' stirring under reflux, the still hot reaction mixture is freed by filtration from the formed ammonium salt. The filtrate is concentrated by evaporation to about ⅓ of the volume. On cooling, there precipitates, in crystalline form, 1-chloro-1-(3',2',2'-trichloroethyl)spiro(3.3)heptan-2-one of the formula

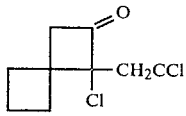

m.p. 93°–94° C.

IR Spectrum (CCl$_4$) in cm$^{-1}$: 1790 (C=O).

NMR Spectrum (100 MHz, CDCl$_3$) in ppm: 1.70–2.80 (m, 6H); 3.15–3.60 (m, 4H).

EXAMPLE 11

2.42 g (0.01 mol) of the 1-(2',2',2'-trichloroethyl)-spiro(3.3)heptan-2-one produced according to Example 10 is placed into 30 ml of methylene chloride, and 2 g (0.012 mol) of m-chloroperbenzoic acid is added. The reaction mixture is subsequently stirred for 48 hours at room temperature (21°–26° C.), filtered, and then washed with methylene chloride. The filtrate is washed with cold (0°–5° C.) sodium carbonate solution and cold (0°–5° C.) water, dried over sodium sulphate and concentrated by evaporation. The residue is recrystallised from diethyl ether/n-hexane to yield 5-(2',2',2'-trichloroethyl)-6-oxaspiro(3.4)octan-7-one of the formula

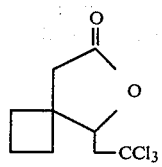

as white crystals, m.p. 86.5°–87.5° C.

IR Spectrum (CHCl$_3$): 1779 (C=O), 1165, 1023 cm$^{-1}$.

$^1$H-NMR Spectrum (CDCl$_3$): 1.7–2.4 (m, 6H, CH$_2$—(1)+CH$_2$—(2)+CH$_2$—(3)); 2.68 (s, 2H, CH$_2$—(8)); 3.05+3.12 (2 d, 2H, CH$_2$—CCl$_3$, J=3 and 6H$_2$); 4.57 (dxd, 1H, CH—(5)).

Analysis for C$_9$H$_{11}$Cl$_3$O$_2$ (molecular weight 257.54). calculated: C 41.97%, H 4.3%, Cl 41.30%. found: C 42.09%, H 4.27%, Cl 41.31%.

EXAMPLE 12

Dry HCl is introduced into 2.57 g (0.01 mol) of the 5-(2',2',2'-trichloroethyl)-6-oxaspiro(3.4)-octan-7-one, produced according to Example 11, in 30 ml of absolute ethanol. After the reaction has subsided (temperature rise up to 55° C.), the reaction mixture is concentrated by evaporation; it is then taken up in absolute ethanol, and 0.011 mol of sodium ethylate (produced from 0.27 g of sodium in ethanol) is added. After a stirring period of 30 minutes, the mixture is concentrated by evaporation; 38 ml (about 0.06 mol) of 10% sodium hydroxide solution is added, and stirring is maintained at 95° C. for 6 hours. After cooling, the mixture is washed with several portions of diethyl ether, acidified with sulphuric acid, and extracted with diethyl ether. The ether extracts after drying over sodium sulphate are concentrated by evaporation. By filtration of the residue from the tenfold amount by weight of silica gel (eluant: hexane/diethyl ether in the volume ratio of 1:1), a small amount of strongly polar impurities is removed. After concentration of the filtrate by evaporation, there is obtained 2-(2',2'-dichlorovinyl)spiro(2.3)hexane-1-carboxylic acid of the formula

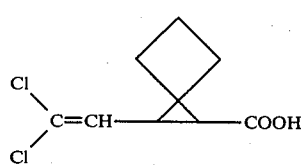

having a melting point of 122°–128° C.

IR Spectrum (CCl$_4$) in ppm$^{-1}$: 1705 (C=O).

NMR Spectrum (100 MHz, CDCl$_3$) in ppm: 1.60–2.60 (m, 8H); 5.34, 5.97 (each a d; together 1H); 11.80–11.50 (broad s, 1H).

EXAMPLE 13

261 g of isobutylene is injected into a 1 liter autoclave containing 49 g (0.23 mol) of 4,4,4-trichlorobutyric acid chloride in 280 ml of cyclohexane. A solution of 28.3 g (0.28 mol) of triethylamine in 233 ml of cyclohexane is pumped in at 70° C. in the course of 4 hours. The reaction mixture is afterwards held at 70° C. for a further 4 hours. The precipitated hydrochloride of the triethylamine is filtered off; the filtrate obtained is washed with dilute hydrochloric acid and then with water, dried over sodium sulphate and concentration by evaporation. Distillation of the residue yields 2-(2',2',2'-trichloroethyl)-3,3-dimethylcyclobutanone as a clear liquid, b.p. 118°–122° C./14 mm Hg.

We claim:

1. A compound of the formula I

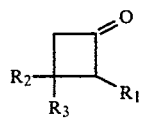

(I)

wherein
- $R_1$ represents —CH=$CX_2$ or —$CH_2$—$CX_3$, and X in each case represents chlorine or bromine,
- one of $R_2$ and $R_3$ represents methyl and the other hydrogen or methyl, or
- $R_2$ and $R_3$ together represent alkylene having 2–4 C atoms.

2. A compound of the formula I according to claim 1, wherein $R_1$ represents —$CH_2CCl_3$ or —CH=$CCl_2$, one of $R_2$ and $R_3$ represents methyl and the other represents hydrogen or methyl, or $R_2$ and $R_3$ together represent alkylene having 2 or 3 C atoms.

* * * * *